United States Patent [19]

Zhu et al.

[11] Patent Number: 5,400,773

[45] Date of Patent: Mar. 28, 1995

[54] INFLATABLE ENDOSCOPIC RETRACTOR

[75] Inventors: Yong H. Zhu, Loma Linda; Wolff M. Kirsch, Redlands, both of Calif.

[73] Assignee: Loma Linda University Medical Center, Loma Linda, Calif.

[21] Appl. No.: 6,250

[22] Filed: Jan. 19, 1993

[51] Int. Cl.⁶ .............................................. A61B 17/00
[52] U.S. Cl. ..................................... 128/20; 606/192
[58] Field of Search ................. 128/20; 606/191, 192, 606/198; 604/104–106

[56] References Cited

U.S. PATENT DOCUMENTS

| | | |
|---|---|---|
| 3,782,370 | 1/1974 | McDonald . |
| 3,863,639 | 2/1975 | Kleaveland . |
| 4,240,433 | 12/1980 | Bordow . |
| 4,312,353 | 1/1982 | Shahbabian . |
| 4,714,074 | 12/1987 | Rey et al. . |
| 4,984,564 | 1/1991 | Yuen . |
| 4,990,139 | 2/1991 | Jang ........................ 606/192 X |
| 5,036,868 | 8/1991 | Berggren et al. ......... 606/192 X |
| 5,156,590 | 10/1992 | Vilmar ........................ 128/4 X |
| 5,163,949 | 11/1992 | Bonutti ........................ 606/192 |
| 5,195,507 | 3/1993 | Bilweis ........................ 606/191 X |
| 5,260,009 | 11/1993 | Penn ........................ 264/40.1 |
| 5,308,327 | 5/1994 | Heaven et al. ........................ 128/20 |

Primary Examiner—Richard J. Apley
Assistant Examiner—Donna Y. Maraglio
Attorney, Agent, or Firm—Knobbe, Martens, Olson & Bear

[57] ABSTRACT

An inflatable endoscopic retractor is disclosed for retracting organs and tissues in the body. The inflatable retractor comprises an inflatable balloon configured to retract specific organs and tissues at the site of the endoscopic procedure, with attached inflation and deflation means. In one embodiment, the inflatable balloon has an attached support rib to provide additional strength and rigidity during retraction. In another embodiment, the inflatable balloon has multiple projections, each with an attached support rib, to provide retraction in several directions. A retractor having an endoscopic housing with separate channels is also disclosed which provides retraction as well as the means for inserting a second endoscopic surgical tool.

7 Claims, 6 Drawing Sheets

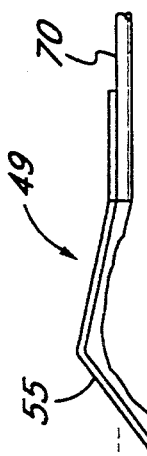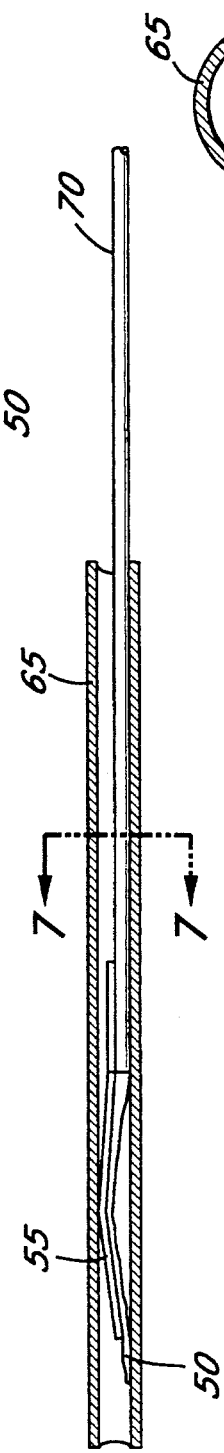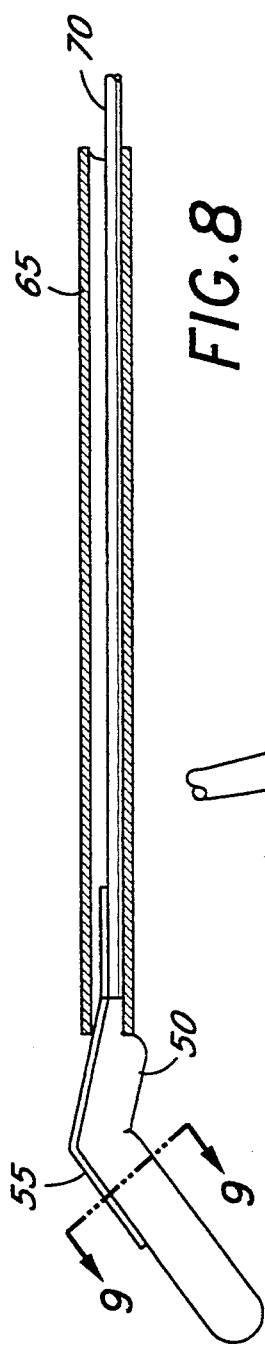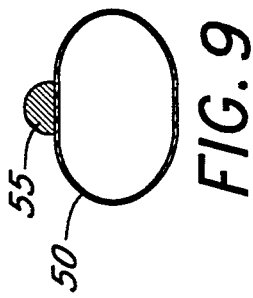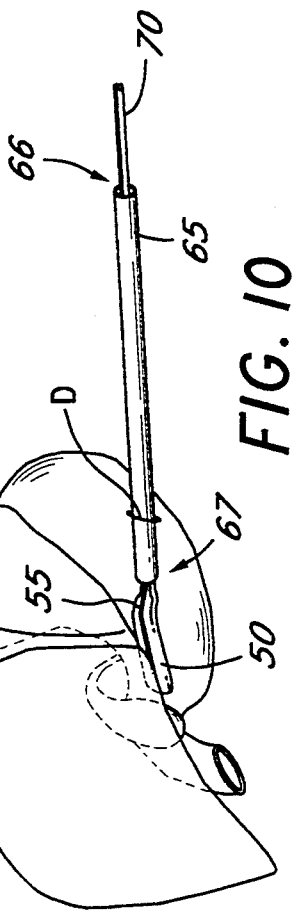

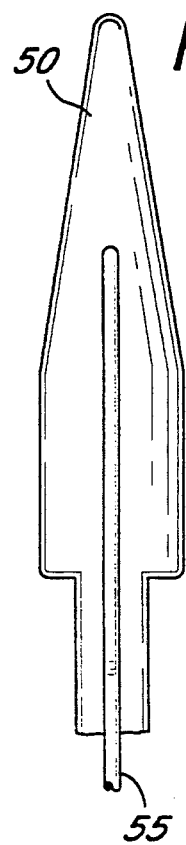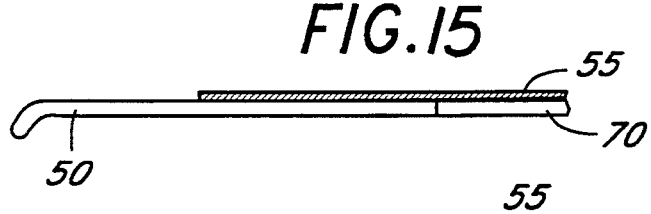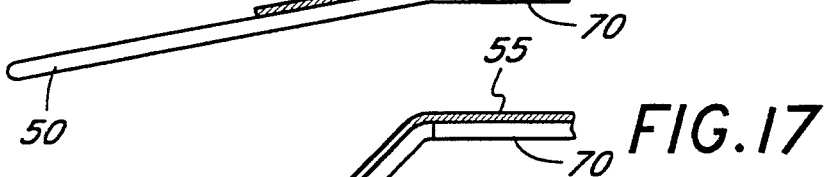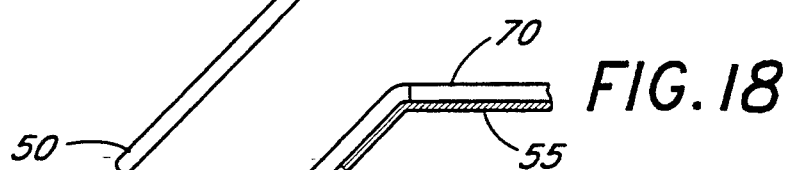

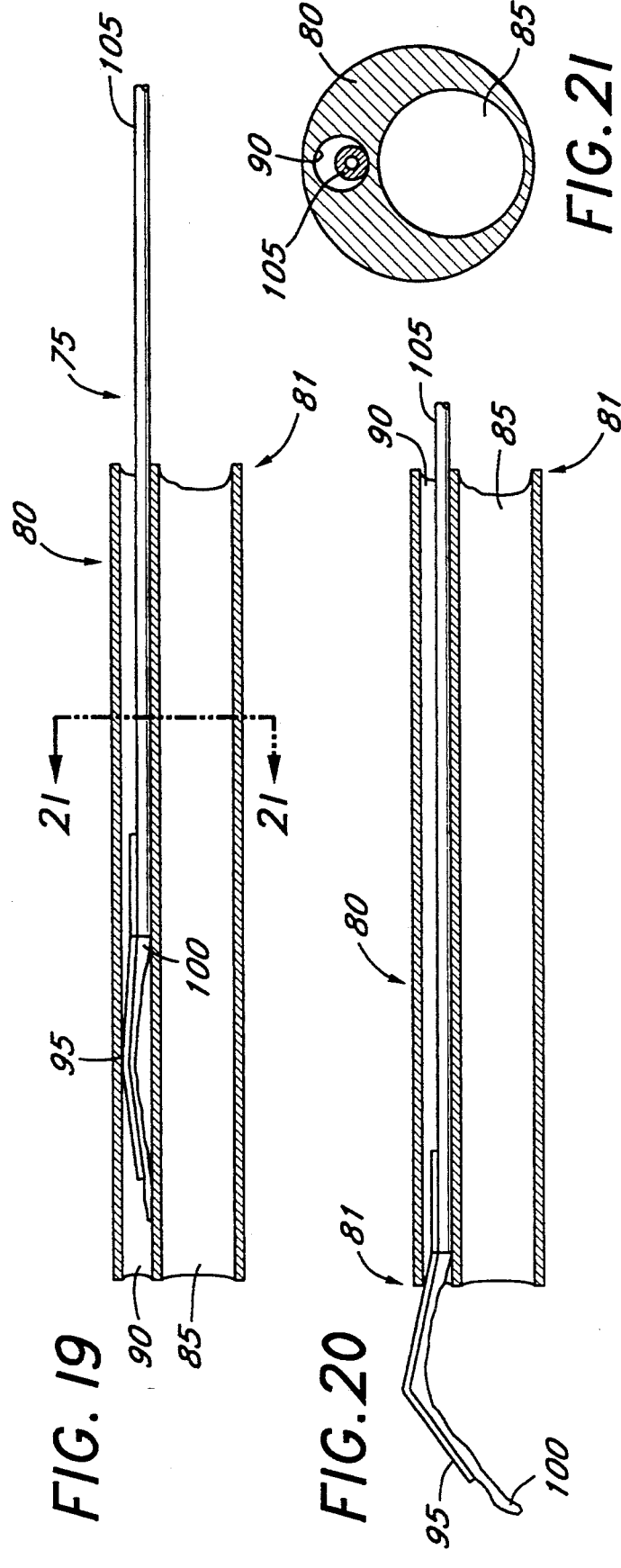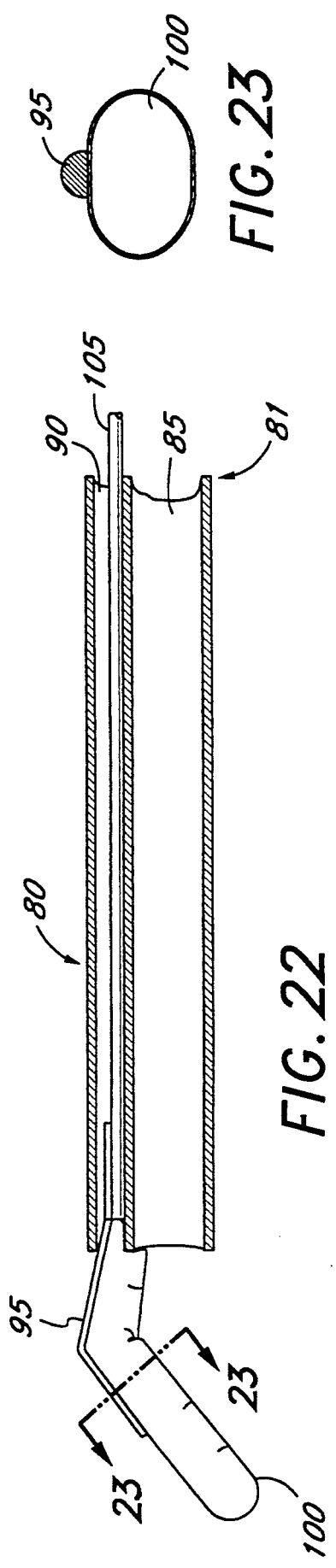

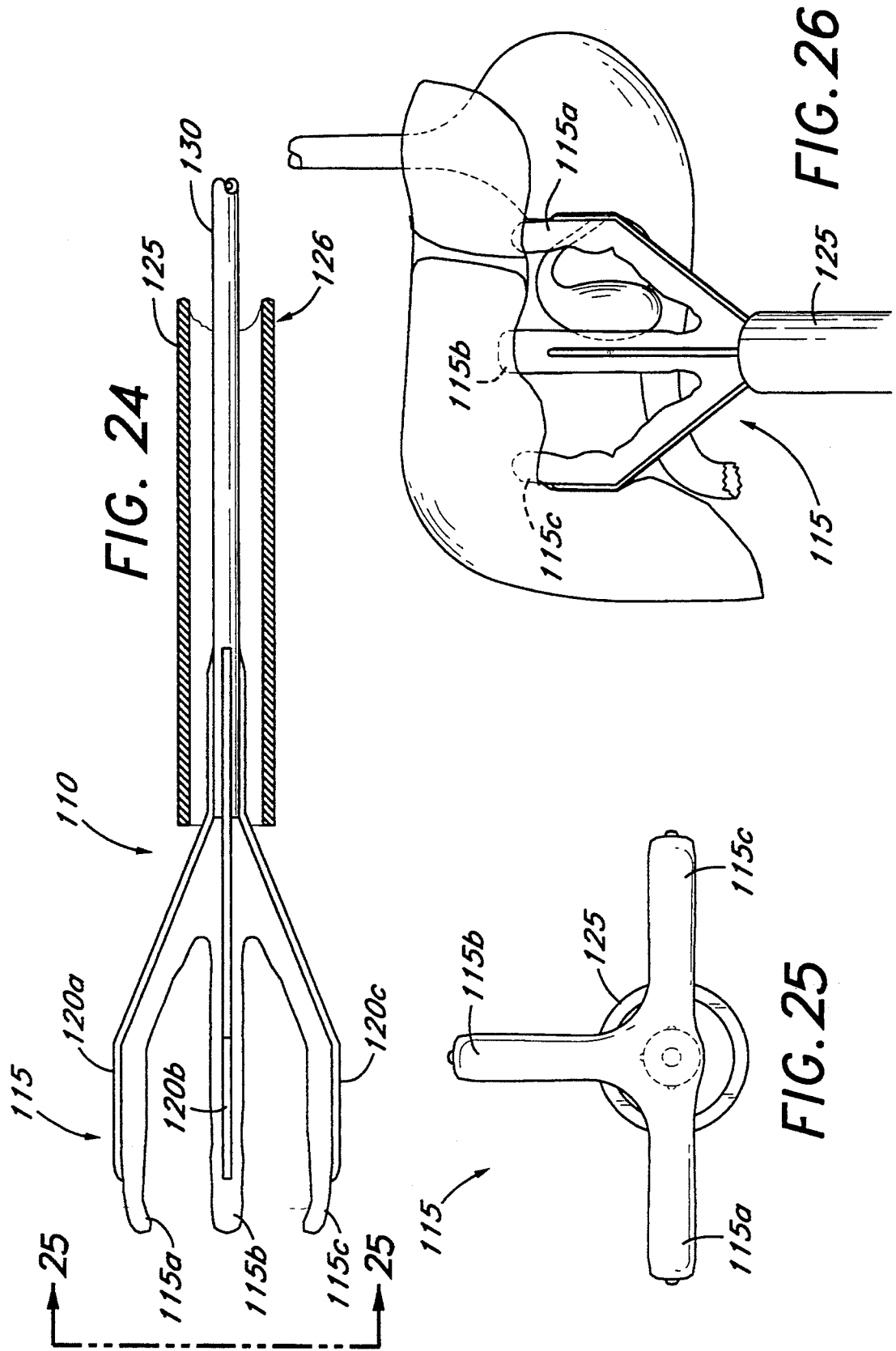

INFLATABLE ENDOSCOPIC RETRACTOR

FIELD OF THE INVENTION

The present invention relates to retractors used in surgery, and more specifically, to an inflatable retractor by which an internal organ or other internal body part may be retracted during endoscopic surgery.

BACKGROUND OF THE INVENTION

The field of endoscopic surgery has been advancing rapidly in recent years. In this form of surgery, procedures are performed inside the body of a patient using instruments inserted through small incisions or ports in the body. The surgery is performed with the aid of an endoscope, which is a thin, tube-like instrument featuring a light source, viewing lenses, and/or various other attachments such as irrigators, scissors, snares, brushes or forceps. Endoscopes may be flexible or rigid, and normally utilize optic fibers to transmit light to the internal cavity. The surgery is normally viewed by the surgeon through an ocular. Lenses are placed near the tip of the endoscope and the image thereon is transmitted via optic fibers or other lens systems to the ocular or viewer. Other types of endoscopes utilize optic fibers to transmit electronic signals representing the internal image from the distal lens to a video monitor which is viewed by the surgeon.

This form of surgery allows internal visualization of the body structure without the necessity of excessive dissection of tissue. Typical endoscopes are in the 5 to 12 mm diameter range and thus require only very small incisions for insertion into the body.

Endoscopic surgery has developed rapidly because of the numerous benefits arising in favor of the patient. Since there is only a small incision to permit the entrance of the endoscope and other endosurgical devices, endoscopic surgery results in less trauma to the patient's body and faster patient recovery. For the benefits of endoscopic surgery to arise, however, all aspects of the surgery, such as the initial examination, retraction of internal organs, and the surgical procedure itself, must be capable of being performed through small endoscopic incisions or ports.

The obvious difficulty associated with endoscopic surgery is inadequate visualization of the internal structure required to properly complete the surgical procedure. Endoscopic surgery is thus difficult in areas which are typically difficult to reach, such as the gallbladder. In the surgical removal of the gallbladder, also known as cholecystectomy, the tissue and organs surrounding the gallbladder are examined using an endoscope and retracted in order to properly expose the organ which is to be removed.

Currently, endoscopic procedures in the abdominal cavity, otherwise known as laparoscopy, often require retraction. Specifically, endoscopic procedures involving the gallbladder entail retracting the liver, which rests directly above the gallbladder. In an open surgery procedure, retraction such as this is relatively easy, as the surgery involves the exposure of the entire abdominal cavity. In order to obtain the benefits of endoscopic surgery, however, a form of retraction which can be accomplished through endoscopic ports is necessary.

In an endoscopic procedure involving the gallbladder or other abdominal organ, retraction is currently accomplished by inflating the peritoneal cavity with carbon dioxide. This method of retraction requires a small endoscopic port for the introduction of the gas source. The gas is introduced into the body through a trocar, and a state of pneumoperitoneum occurs. The gas inflates the peritoneal cavity so as to cause the skin and muscles to separate from and rise above various organs and tissue, creating the exposure necessary to accomplish the endoscopic surgery.

Several problems are associated with pneumoperitoneal retraction however. First of all, exposure of the organs remains adequate only while the required pneumoperitoneal state remains. Since endoscopic surgery normally requires the introduction of at least the endoscope, and more often several other endoscopic instruments, several endoscopic ports will most likely be created in the patient's body. Each of these ports, which normally use a cannula to keep them open for access, in effect create an exhaust port for the gas. The risk that insufflation pressure may be lost increases the risk that the endoscopic procedure may go awry as adequate exposure for the endoscope is eliminated.

Further, there are many complications which are associated with persistent pneumoperitoneum during an endoscopic procedure. Acute cardiovascular collapse secondary to over-distension of the abdomen, vasovagal reflex activation, cardiac arrhythmia, pneumothorax, subcutaneous emphysema, alteration of large vein venous return, retinal hemorrhage, blindness, carbon dioxide embolism, and general patient discomfort have all been associated with persistent pneumoperitoneum.

In addition, pneumoperitoneal retraction is effective in retracting only the muscles and tissue from above the organs. The organs themselves are not, to a great extent, retracted from each other.

Lastly, current mechanical retractors are often made of stainless steel or other metals. Use of metal retractors in the presence of other endoscopic surgical tools may result in inadvertent electrical or laser injury. Additionally, such retractors can cause inadvertent tearing, slicing, puncture or other mechanical injury to the internal tissues and organs.

There is therefore a need for a device and method which provide retraction in conjunction with endoscopic procedures which is effective in providing adequate visualization and which is safe and has fewer side effects than current retraction methods.

SUMMARY OF THE INVENTION

The present invention provides an apparatus and method for improved endoscopic retraction procedures. The invention permits safe and effective retraction of internal organs and tissue during an endoscopic procedure.

Retraction is accomplished with the present invention through the use of an inflatable bladder or balloon inserted through an endoscopic housing. The balloon is soft and flexible enough to avoid damage to internal organs and tissues, yet it is sufficiently inelastic and rigid so as to provide retraction when inflated.

In accordance with one aspect of the present invention, there is provided an inflatable endoscopic retractor comprised of an inflatable balloon having an anatomical configuration designed to retract structures specific to the surgical procedure. For example, the balloon for use in an endoscopic cholecystectomy would be configured to retract the liver, as well as to protect the retracted liver and bowel. Analogous anatomical balloons for use in laparoscopic surgery include configurations for the kidney, bladder, pancreas, and other abdominal exposures.

This balloon is fabricated using an anatomical model of the human abdominal cavity or other areas of the body. This model can be based upon MRI or CT scan images of a particular patient, or the known internal structure of a normal adult. Using the anatomical model, the balloon is configured to retract and support the desired anatomical structure upon inflation.

When retraction during laparoscopic surgery is desired, the deflated balloon is inserted into the body through an endoscopic tube or housing. The balloon is slightly inflated to assist in its proper positioning inside the body, and endoscopic forceps may be used to assist in accomplishing such positioning. Once the balloon is in place, it is inflated with air or other gas or liquid, in an amount sufficient to retract the desired organ or other tissue and maintain and support the organ or tissue in its retracted position. After the endoscopic procedure is complete, the balloon is deflated and drawn through the endoscopic housing, and the housing is removed.

In accordance with a second aspect of the present invention, there is provided an inflatable endoscopic retractor comprised of an inflatable balloon attached to a support rib that provides some strength and rigidity for the retraction, without damaging the retracted tissues. This support rib is pre-bent such that the rib forms an angle. The rib is constructed of material which is sufficiently flexible to allow the rib to straighten upon insertion of the rib into the endoscopic housing, yet rigid enough to spring back into its angled position upon exiting the housing. This spring bias or "give" in the retraction also provides a measure of safety for the retracted tissues. The inflatable balloon, which is attached to the support rib, can have any of a number of configurations, including, for example, a spatula-like structure.

When retraction is desired, the retractor is inserted into the body through an endoscopic housing or appropriate cannula. Once in position, the balloon is inflated with air or other gas or liquid in an amount sufficient to retract the desired organ or other tissue and maintain and support the organ or tissue in its retracted position. When the endoscopic procedure is complete, the balloon is deflated and withdrawn through the housing, and the housing is removed from the patient's body. Two or more of these inflatable retractors can be inserted into a single endoscopic housing to achieve the desired retraction and support.

In accordance with another aspect of the present invention, there is provided a method of retracting internal tissue and organs using a retractor having an elongated housing capable of being inserted into the body. This housing has two separate channels. The first channel is used to guide the entry of the inflatable balloon and its attached support rib. The second channel is used to guide the insertion of any of a number of endoscopic instruments. Thus, the present invention provides a single instrument inserted through a single endosurgical port which provides retraction, as well as providing a channel for the insertion of a second surgical tool.

In accordance with still another aspect of the present invention, there is provided an inflatable endoscopic retractor comprised of an inflatable balloon having multiple fingers or projections, with each projection attached to an angled support rib that provides strength for the retraction. The retractor is inserted into the body through an endoscopic housing. Once in position, the balloon is inflated with air or other gas or liquid in an amount sufficient to retract the desired organ or other tissue and maintain and support the organ or tissue in its retracted position. When the endoscopic procedure is complete, the balloon is deflated and withdrawn through the endoscopic housing, and the housing is removed from the patient's body.

The inflatable endoscopic retractor of the present invention significantly reduces the risks associated with retraction, such as thermal, electrical, or mechanical injury. In addition, it does not present the dangers associated with continuous pneumoperitoneal retraction. The present invention can be positioned with only initial insufflation to provide easy insertion of the device. After insertion, retraction can be maintained simply and safely with the inflatable balloon.

The inflatable retractor is advantageously very small, which allows its introduction into the body through a housing placed in a small trocar opening. The retractor is normally introduced through a single small opening.

The inflatable retractor is much more effective in retracting organs, especially larger ones, than insufflation. The invention allows the surgeon or assistant to manually retract an organ to the extent necessary, merely by manipulating the retractor, and/or the inflation pressure inside the balloon. The inflatable retractor is easily manipulable into a variety of angles and positions to provide exact retraction at any location. This is in contrast to the insufflation method, where the gas indiscriminately fills the body cavity. On the other hand, if desired, the present retractor can be used in conjunction with insufflation as it is compatible with that method.

BRIEF DESCRIPTION OF THE DRAWINGS

FIG. 5 is a side view of a second embodiment of the inflatable retractor of the present invention, showing the support rib in an angled position prior to its insertion into the endoscopic housing, the deflated balloon attached to the support rib, the inflation and deflation tube attached to the balloon, and the endoscopic housing shown in cross section.

FIG. 6 is a side view similar to FIG. 5, but shows the support rib and the attached deflated balloon inserted into the endoscopic housing.

FIG. 7 shows a cross-section of the inflation and deflation tube inside the endoscopic housing taken along the line 7—7 in FIG. 6.

FIG. 8 shows a side view of the second embodiment of the inflatable retractor of the present invention after its exit from the endoscopic housing, showing the support rib in an angled position, the inflated balloon at- FIG. 9 is a cross-section of the balloon and its attached support rib taken along the line 9—9 in FIG. 8, showing the balloon inflated.

FIG. 10 is a schematic view of the second embodiment of the inflatable retractor of the present invention, with the balloon inflated and retracting the liver.

FIG. 11 is a top plan view of an embodiment of the inflatable balloon of the present invention, showing its tapered shape.

FIG. 12 is a top plan view of a second embodiment of the inflatable balloon of the present invention, showing its rectangular shape.

FIG. 13 is a side view of the balloon of FIG. 12, showing its curved tip.

FIG. 14 is a top plan view of a third embodiment of the inflatable balloon of the present invention, showing its thin rectangular shape and rounded tip.

FIG. 15 is a side view of an embodiment of the balloon of the present invention, showing the support rib at a 180 degree angle, and the balloon attached to the bottom of the support rib.

FIG. 16 is a side view of an embodiment of the balloon of the present invention, showing the support rib at a 190 degree angle, and the balloon attached to the bottom of the support rib.

FIG. 17 is a side view of an embodiment of the balloon of the present invention, showing the support rib at a 225 degree angle, and the balloon attached to the bottom of the support rib.

FIG. 18 is a side view of an embodiment of the balloon of the present invention, showing the support rib at a 225 degree angle, and the balloon attached to the top of support rib.

FIG. 19 is a side view of a third embodiment of the inflatable retractor of the present invention, showing an endoscopic housing having 2 separate chambers in cross section, and the retractor having a support rib with attached balloon inserted in the first hollow chamber.

FIG. 20 is a side view of the third embodiment of the inflatable retractor of the present invention similar to FIG. 19, but showing the support rib with attached balloon exiting the housing.

FIG. 21 is a cross-sectional view of the endoscopic housing taken along line 21—21 in FIG. 19, showing the 2 adjacent chambers and the inflation and deflation tube.

FIG. 22 is a side view of the third embodiment of the inflatable retractor of the present invention similar to FIG. 20, but showing the balloon inflated.

FIG. 23 is a cross-sectional view taken along the line 23—23 in FIG. 22, showing the inflated balloon and its attached support rib.

FIG. 24 is a side view of a fourth embodiment of the present invention showing a single balloon having multiple projections, each projection having its own angled support rib, an inflation and deflation tube attached to the balloon, and the endoscopic housing shown in cross section.

FIG. 25 is an end view of the multiple projections of the inflatable balloon taken along the line 25—25 in FIG. 24.

FIG. 26 is a schematic view of the fourth embodiment of the present invention, showing the multiple projections being used to retract the liver and expose the gall bladder.

DETAILED DESCRIPTION OF THE INVENTION

Figure 1:
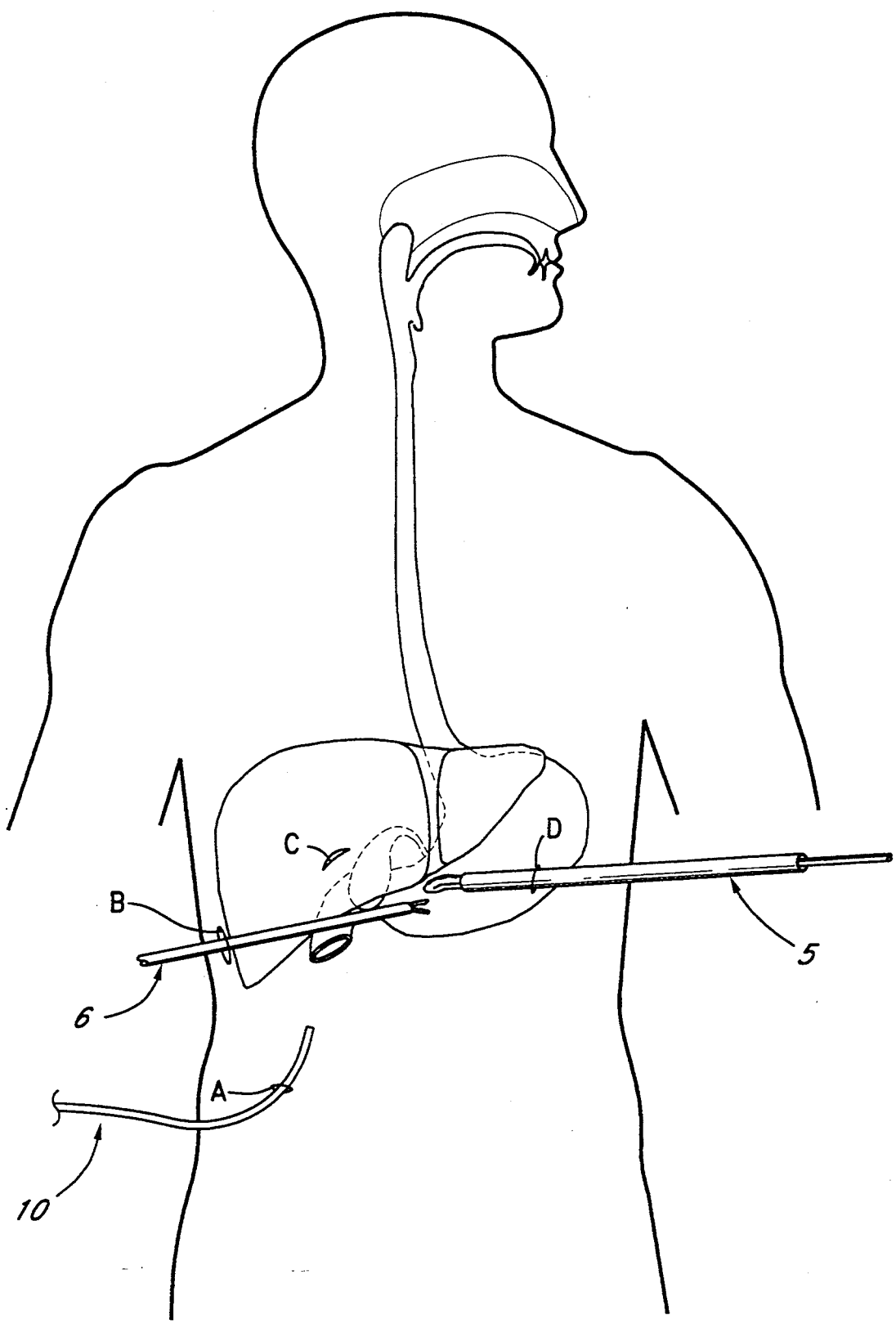
FIG. 1 is a schematic view of a patient illustrating the general manner in which the inflatable retractor of the present invention may be used during an endoscopic procedure.

Referring to FIG. 1, there is shown a schematic view of a patient undergoing an endoscopic cholecystectomy, illustrating only one example in which the inflatable retractor 5 of the present invention might be utilized during endoscopic surgery. A small endosurgical port A is shown, through which an endoscope 10 is inserted. This allows the surgeon to view the internal tissues and organs in the surgical area. Other surgical devices (not shown) may be inserted through a similar surgical port C in order to perform the desired procedure.

The retractor 5 of the present invention is inserted through a small opening or port D made in the patient's body. A pair of endosurgical forceps may be inserted through another surgical port B to aid in the positioning of the endoscopic inflatable retractor 5.

As illustrated, the inflatable retractor is used to constrain and retract the liver to permit the endosurgical removal of the gallbladder. It should be noted, however, that the principles of the present invention are not limited to any particular surgical procedure but may be applied to a wide variety of procedures and applications, including open surgery.

Figure 2:
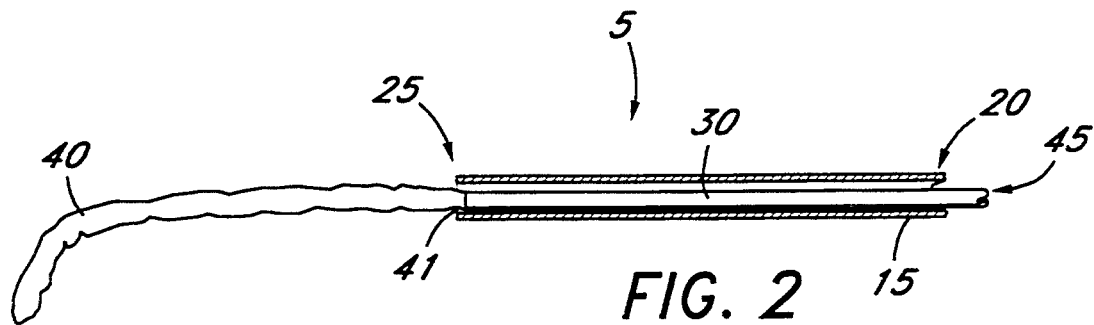
FIG. 2 is a side view of a first embodiment of the inflatable retractor of the present invention with the endoscopic housing shown in cross section.
Figure 3:
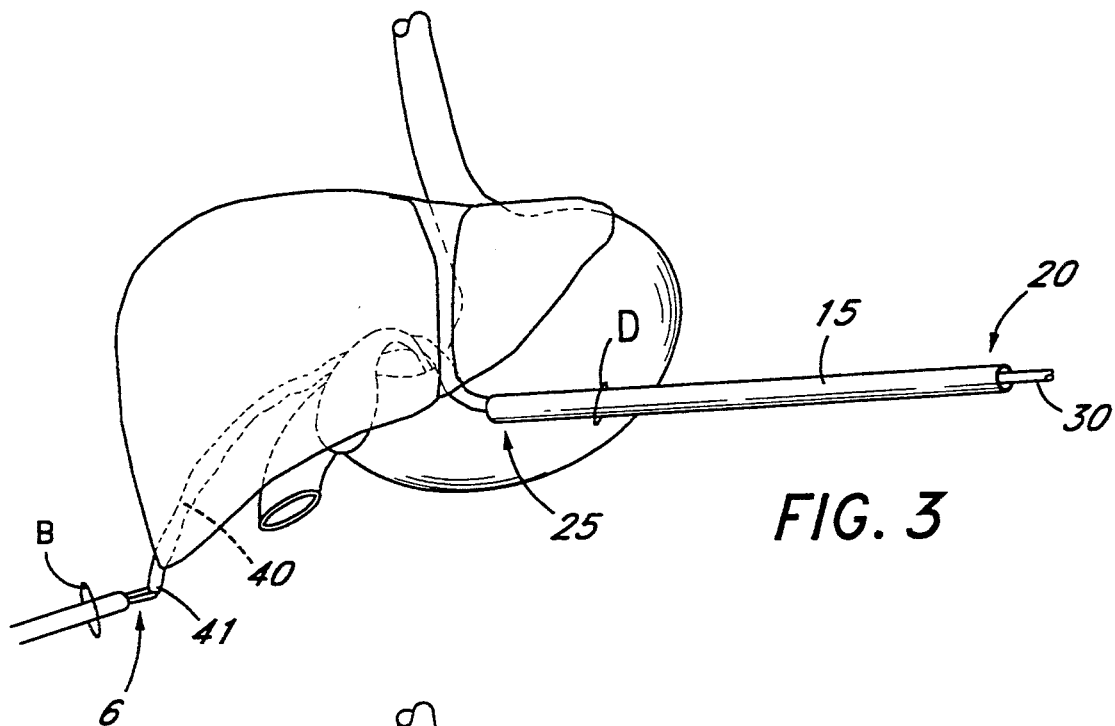
FIG. 3 is a schematic view of the first embodiment of the inflatable retractor of the present invention, showing it positioned beneath the liver, with the balloon deflated.
Figure 4:
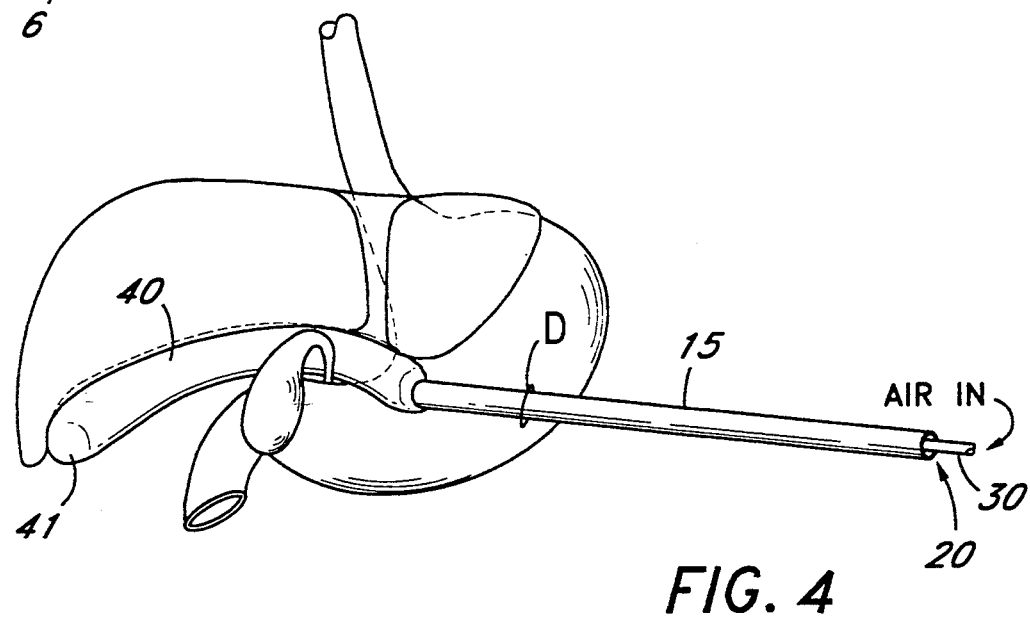
FIG. 4 is a schematic view of the first embodiment of the inflatable retractor of the present invention similar to FIG. 3, but with the balloon inflated and retracting the liver so as to expose the gall bladder.

Referring now to FIGS. 2-4, there is shown one embodiment of the endoscopic inflatable retractor 5 of the present invention. FIG. 2 illustrates the retractor 5 within a housing 15 suitable for use in endoscopic procedures. The length of the housing 15 is primarily dependent upon the type of procedure in which the retractor is to be used.

The housing 15 has a proximal or control end 20, and a distal or insertion end 25. The housing 15 is preferably made of a material, such as stainless steel, which will remain free from degradation, is easily sterilized, and is biocompatible. The shape of the distal end 25 is chosen to aid in preventing the puncture or other injury to internal organs and tissue when the housing 15 is being manipulated inside the patient's body. The proximal end 20 remains outside the patient's body during the procedure.

In addition to the cannula-like housing shown in FIGS. 2-4, the present invention is also compatible with standard trocar-induced cannulas frequently utilized in endoscopic surgery. Such cannulas provide a port into the patient's body and a short tube for the insertion of endoscopic instruments. Thus, the principles of the present invention are not to be limited to any particular housing, cannula, or method of insertion into the patient's body.

Still referring to FIG. 2, the inflatable retractor 5 consists of an long, inflatable balloon 40 with an anatomical configuration designed to retract structures specific to the surgical procedure. The balloon 40 is comprised of a soft, flexible material which preferably does not absorb liquid and is easily sterilized, such as rubber, vinyl, polyethylene, or other polymeric material.

The balloon 40 of the inflatable retractor 5 is fabricated based upon MRI or CT scan three-dimensional images of the area involved in the surgery. An anatomical model of the internal structure to be retracted is constructed based upon these three-dimensional images. This model is used to construct a premolded, prevulcanized, or prefabricated three-dimensional balloon 40 to conform to that anatomical model. In this way, the retractors 5 can be fabricated to fit a variety of anatomical configurations, and the surgeon can choose the retractor 5 which best fits his needs during the endoscopic procedure.

Alternatively, the retractor 5 can be configured based upon MRI or CT scan three-dimensional images of the anatomical structure of a particular patient. An anatomical model of the internal structure of the patient is constructed based upon the three-dimensional images. Using the model, the three-dimensional balloon 40 is fabricated to conform to the internal structures to be retracted. In this manner, a custom designed retractor can be manufactured for use with a particular patient.

Referring again to FIG. 2, there is shown a small-diameter hollow tube 30 made of non-collapsible, flexible material which is connected to the inflatable balloon 40 at the balloon's proximal end 41. This hollow tube 30 permits the entry and exit of gas or liquid to and from the inflatable balloon 40. The proximal end of the tube 45 connects to an inflation and venting device (not shown). This device can be any of a variety of devices, including, for example, a bulb-type or piston-type syringe, a gas cartridge, or a fluid pump.

OPERATION OF THE RETRACTOR

The operation of the inflatable endoscopic retractor as used in a cholecystectomy procedure will now be explained, as illustrated in FIGS. 3 and 4. The body is first prepared by introducing a state of pneumoperitoneum to aid in the placement of the inflatable retractor 5. The endoscopic housing 15 is inserted into an endosurgical port D in the patient's body. An endoscope (not shown) may also be inserted into the body to aid in visualizing the internal structures and to ensure the proper positioning of the inflatable retractor 5. A pair of forceps 6 suitable for use in endoscopic surgery may be inserted into a different endosurgical port B to aid in the positioning of the retractor 5.

As illustrated in FIG. 3, the balloon of the inflatable retractor 40 is inserted into the proximal end of the endoscopic housing 20 and pushed through using the inflation/deflation tube 30 until it emerges from the distal end of the housing 25 into the patient's body. The balloon 40 may be slightly inflated to aid in its maneuvering. As the balloon 40 emerges from the distal end of the housing 25, it can be positioned by either continuing to push the slightly inflated balloon 40 through the housing 25, or by inserting a pair of forceps 6 through a second endosurgical port B in the patient's body. The forceps are used to grasp the distal end of the inflatable balloon 41 and pull the balloon 40 through the endoscopic housing 15 and into the desired position.

Referring now to FIG. 4, once the inflatable balloon 40 is in the desired position, gas or liquid is introduced into the balloon 40 through the hollow tube 30. As the balloon 40 inflates, it lifts and supports the liver so as to expose the gallbladder. At this time, the retraction, as necessary for procedures involving the gallbladder, will be sufficient, and the condition of pneumoperitoneum may be allowed to lapse. If desired, some insufflation may still be used along with the retractor of the present invention to provide additional working space within the abdominal cavity. The procedure involving the gallbladder may then be successfully completed.

After the procedure has been completed, the balloon 40 is deflated by allowing the gas or liquid to exit the balloon 40 through the hollow tube 30. The deflated balloon 40 is then removed from the body by pulling the tube 30 away from the proximal end of the housing 20, thus drawing the balloon 40 through the housing 15 and out of the patient's body. The housing 15 itself may then be removed and the endosurgical port D sutured closed.

RETRACTOR WITH SUPPORT RIB

Referring now to FIGS. 5-9, there is shown an alternative preferred embodiment of the retractor 49 of the present invention. The inflatable balloon 50 is attached to a support rib 55, which is bent at angle as illustrated in FIG. 5. The balloon 50 and the support rib 55 may be joined during the molding of the balloon 50, such that the balloon 50 is molded around the support rib 55. The rib 55 may also be joined to the outside surface of the balloon 50 using an adhesive. Others means of joining the balloon 50 and support rib 55 will be readily apparent to one of ordinary skill in the art.

The support rib 55 may have various configurations in order to provide varying degrees of control and manipulation during retraction. For example, in cross-section, the rib 55 may be circular, square, or rectangular in shape. In addition, the rib may have various length and width dimensions in order to vary the degree of rigidity of the retractor. The rib 55 is preferably made of material such as spring steel, which is flexible enough to allow the angled rib 55 to straighten upon insertion of the rib 55 into an endoscopic housing 65 (FIG. 6), yet rigid enough to spring back into its bent position and manipulate and support the desired internal organ upon exit from the housing 65 (FIG. 8). The angle of the rib 55 may be fixed, or it may be adjustable. This adjustability would at the time of use, allow the surgeon to manually or mechanically adjust the degree of the angle as well as the direction of the angle outside the patient's body prior to insertion of the retractor, after viewing the area to be retracted with an endoscope. This allows the surgeon to adjust the retractor to fit his needs during the procedure.

The inflatable balloon 50 is attached to the support rib 55 and to a hollow tube 70 used to inflate and deflate the balloon, as well as to push the retractor 49 through the distal end of the housing 65 and position the retractor 49 inside the patient's body. As shown in FIG. 7, the hollow tube 70 fits within the endoscopic housing 65, and has a space 71 through which gas or liquid passes during inflation or deflation of the balloon. As shown in FIG. 8, the hollow tube 70 also assists in both supporting and positioning the inflatable balloon 50 inside the body.

The operation of the inflatable retractor as used in a cholecystectomy will now be explained with reference to FIG. 10. The endoscopic housing 65 is inserted into an endosurgical port D in the patient's body. The balloon 50 and its attached support rib 55 are inserted into the proximal end of the housing 66 and pushed through the distal end of the housing 67 and into the desired position using the hollow tube 70 attached to the balloon 50.

Once the inflatable retractor 49 is in the desired position beneath the liver, as shown in FIG. 10, air or other gas or liquid is introduced into the balloon 50 through the hollow tube 70 causing the balloon 50 to inflate. FIG. 9 illustrates the inflated balloon 50 with its attached support rib 55 in cross-section.

As shown in FIG. 10, the inflation of the balloon 50 lifts and supports the liver, exposing the gallbladder. At this time, the retraction, as necessary for procedures involving the gallbladder, will be sufficient and the procedure involving the gallbladder may then be completed.

After the procedure is completed, the balloon 50 is deflated by allowing the fluid inside the balloon 50 to exit through the tube 70. The deflated balloon 50 is then removed from the body by pulling the hollow tube 70 away from the proximal end of the housing 66, thus drawing the balloon 50 through the housing 65 and out of the patient's body. The housing 65 itself can then be removed and the endosurgical port sutured closed.

In accordance with another aspect of the present invention, multiple inflatable retractors as described above can be inserted through a single endoscopic housing. Each retractor can be separately positioned, inflated and deflated to achieve the desired retraction.

As seen in FIGS. 11-18, the ribbed inflatable balloon 50 of the present invention may be configured in several different ways, and the support ribs 55 may be bent at various angles. FIG. 11 illustrates a balloon 50 having a narrow, tapered end. FIG. 12 illustrates a rectangular, spatula-shaped balloon 50. This balloon 50 is shown in a side view in FIG. 13, which depicts its curved distal end. FIG. 14 illustrates a narrow balloon 50. FIGS. 15-18 show the inflatable balloon 50, the attached hollow tube 70, and the various angles at which the support rib 55 may be bent.

RETRACTOR AND CHAMBERED ENDOSCOPIC HOUSING

In another embodiment of the present invention, illustrated in FIGS. 19-23, the inflatable retractor 75 may be used in conjunction with a separate endoscopic instrument. A single endoscopic housing 80 having two separate hollow chambers 85 and 90 is used. The inflatable retractor 75 is inserted into the first hollow chamber 90. The housing 80 and the inflation/deflation tube of the inflatable retractor 75 are seen in cross-section in FIG. 21. An endoscope or other endosurgical device (not shown) may be inserted into the second hollow chamber 85.

The operation of this embodiment of the present invention will now be explained in connection with FIGS. 19-23. The endoscopic housing 80 is inserted into an endosurgical port in the patient's body. As shown in FIGS. 19 and 20, the inflatable retractor 75 is pushed through the housing 80 using the hollow inflation/deflation tube 105 attached to the balloon 100. The hollow tube 105 is used to position the balloon 100 inside the body. Once in position, fluid is forced through the hollow tube 105 and into the inflatable balloon 100 causing it to inflate.

Once inflated, as illustrated in FIG. 22, the balloon 100 can be used to retract the desired organ or tissue within the body. The inflated balloon 100 and its attached support rib 95 are seen in cross-section in FIG. 23. The retraction aids in clearing the area in which the endosurgical procedure is to be performed. A second endosurgical instrument may then be inserted into the body using the second hollow chamber 85 in the endoscopic housing 80. Thus, a single endosurgical port can be used to insert both a retractor to retract any obstructing tissue or organs, and any additional endosurgical instrument required during the procedure.

After the procedure has been completed, the balloon 100 is deflated by allowing the fluid to exit the balloon 100 through the hollow tube 105. The deflated balloon 100 is then removed from the body by pulling the hollow tube 105 away from the proximal end housing 81, thus drawing the balloon 100 through the housing 80 and out of the patient's body. The housing 80 itself is then removed, and the endosurgical port sutured closed.

RETRACTOR WITH MULTIPLE PROJECTIONS

In accordance with another embodiment of the present invention, illustrated in FIGS. 24-26, there is provided an inflatable retractor 110 having an inflatable balloon 115 with multiple inflatable projections 115a-c, each with its own attached angled support rib 120a-c. Each rib 120a-c is preferably made of material such as spring steel, which is flexible enough to allow each angled rib 120a-c to straighten upon insertion into an endoscopic housing 125, yet is rigid enough to spring back into its angled position and manipulate and support the desired internal organ upon exit from the housing 125. The angle of the ribs 120a-c may be fixed or it may be adjustable.

As shown in FIG. 24, a small-diameter hollow tube 130 made of non-collapsible material is connected to the inflatable balloon 115. This tube 130 permits the entry and exit of fluid to and from the balloon 115, and is used to push the retractor 110 through the housing 125 and position the retractor 110 inside the body.

The operation of this embodiment of the present invention will now be explained in connection with FIGS. 24-26. The endoscopic housing 125 is inserted into an endosurgical port in the patient's body. The inflatable retractor 100 is pushed through the housing 125 using the hollow tube 130 attached to the balloon 115. The hollow tube 130 is also used to position the balloon 115 inside the body.

Once the retractor 110 is properly positioned, fluid is introduced into the ballon 115 through the hollow tube 130, causing each of the projections 115a-c to inflate. An end view of the inflated balloon 115 is illustrated in FIG. 25.

As seen in FIG. 26, the inflated balloon 115 lifts and supports the liver, exposing the gallbladder. At this time, the retraction, as necessary for procedures involving the gallbladder, will be sufficient, and the procedure involving the gallbladder may then be completed.

After the procedure has been completed, the balloon 115 is deflated by allowing the fluid inside the balloon to exit through the hollow tube 130. The deflated balloon 115 is then removed from the body by pulling the hollow tube 130 away from the proximal end of the housing 126, thus drawing the balloon 115 through the housing 125 and out of the patient's body. The housing 125 itself may then be removed and the endosurgical port used for insertion may be sutured closed.

Although this invention has been described in terms of certain preferred embodiments and examples, it is intended that the scope of this invention not be limited to the specific embodiments set forth herein. Accordingly, the scope of the invention is intended to be defined only by the claims which follow.

We claim:

1. An inflatable retractor adapted for use in endoscopic surgery, comprising:

an outer elongated rigid cannula for insertion into the body of a patient;

a non-collapsible inner tube having a distal end and a proximal end, said inner tube being capable of being inserted into said cannula such that a portion of said proximal end of said inner tube remains outside the patient's body and a space remains between said inner tube and said cannula to allow manipulation of said inner tube within said cannula;

an inflatable finger-shaped balloon having a longitudinal axis mounted on the distal end of said inner tube, capable of being inserted into said cannula in a collapsed position and supported and positioned by said inner tube upon manipulation of said tube within said cannula; and a metallic support rib mounted axially and externally along said balloon and along at least a portion of the distal end of said inner tube, said support rib being capable of being manipulated into a first bent position which is at an angle to the axis of said balloon, but adapted to straighten upon insertion into said cannula and spring back into said first bent position upon exiting said cannula, and wherein said balloon is attached to said support rib such that said balloon maintains an angled position when outside of said cannula and inflated.

2. The inflatable retractor of claim 1, wherein said outer elongated cannula further comprises:
a first and second hollow channel, wherein said first hollow channel acts as a guide for the insertion of an endoscopic surgical tool into the patient's body and said second hollow channel acts as a guide for said inner tube and said balloon.

3. A method of retracting tissue and organs inside the body of a patient during endoscopic surgery using one or more inflatable retractors, each retractor comprising a non-collapsible tube having a distal end and a proximal end, an inflatable finger-shaped balloon having a longitudinal axis mounted on said distal end of said non-collapsible tube, a metallic support rib mounted axially and externally along said balloon and along at least a portion of the distal end of said tube, said support rib being capable of being manipulated into a first bent position which is at an angle to the axis of said balloon prior to insertion of said balloon into an outer elongated rigid cannula, but adapted to straighten upon insertion into said cannula and spring back into said first bent position upon exiting said cannula, and wherein said balloon is attached to said support rib such that said balloon maintains an angled position when outside of said cannula and inflated, said method comprising:
inserting said outer elongated rigid cannula having a distal end and a proximal end into the body of the patient;
manipulating said support rib into a position at an angle to the axis of the balloon;
inserting said non-collapsible tube and support rib and balloon into said cannula such that the support rib and balloon pass through the cannula and past the distal end of the cannula causing said support rib to return to its bent position thereby causing the attached balloon to assume a bent position by allowing the support rib to act on the attached balloon, and whereby a portion of said inner tube remains outside the body of the patient, and a space remains between said inner tube and said cannula to allow manipulation of said inner tube within said cannula;
positioning said retractor by maneuvering the non-collapsible inner tube; and
inflating said balloon by forcing gas or liquid into said inflatable balloon thereby allowing said balloon to be used to manipulate the patient's tissue and organs thereby creating a space in the body for performing surgery.

4. An inflatable retractor adapted for use in endoscopic surgery, comprising:
an outer elongated rigid cannula for insertion into a patient's body;
an elongate inflatable balloon having a longitudinal axis and sized so as to be capable of passing through said cannula when deflated;
a non-collapsible inner tube having a distal end and a proximal end and having a passageway formed axially therethrough, said inner tube being longitudinally sized to be inserted into said cannula such that said proximal end of said inner tube remains outside the patient's body, and said inner tube being cross-sectionally sized such that a space remains between said inner tube and said cannula;
said distal end of said inner tube being attached to said balloon whereby said balloon may be inflated by the passage of air or gas through said passageway formed in said tube, said distal end of said inner tube positioning said balloon within the body of the patient; and
a manually bendable support rib having a distal end mounted externally along the axis of said balloon, and said support rib having a proximal end rigidly mounted on the distal end of said tube;
whereby said balloon, following inflation, may be manually manipulated by said proximal end of said inner tube and within said space in order to retract organs and tissues inside the patient's body.

5. The inflatable retractor of claim 4, wherein said manually bendable support rib is capable of being manipulated into a first bent position which is at an angle to the axis of said balloon, but adapted to straighten upon insertion into said cannula and spring back into said first bent position upon exiting said cannula, and wherein said support rib is mounted on said balloon such that said balloon maintains an angled position when outside of said cannula and inflated.

6. The inflatable retractor of claim 4, wherein said manually bendable support rib is made of metal.

7. The inflatable retractor of claim 4, wherein said inner tube is flexible.

* * * * *